(12) United States Patent
Coleman et al.

(10) Patent No.: US 9,663,762 B2
(45) Date of Patent: May 30, 2017

(54) METHODS FOR OBTAINING TARGET CELLS

(71) Applicants: Michael Coleman, Houston, TX (US); Jody Vykoukal, Houston, TX (US)

(72) Inventors: Michael Coleman, Houston, TX (US); Jody Vykoukal, Houston, TX (US)

(73) Assignee: Ingeneron, Inc., Houston, TX (US)

( * ) Notice: Subject to any disclaimer, the term of this patent is extended or adjusted under 35 U.S.C. 154(b) by 0 days.

(21) Appl. No.: 13/896,246

(22) Filed: May 16, 2013

(65) Prior Publication Data

US 2013/0252336 A1    Sep. 26, 2013

Related U.S. Application Data

(63) Continuation of application No. PCT/US2011/060984, filed on Nov. 16, 2011.

(60) Provisional application No. 61/414,329, filed on Nov. 16, 2010.

(51) Int. Cl.
*C12N 5/078* (2010.01)
*G01N 33/569* (2006.01)

(52) U.S. Cl.
CPC ..... *C12N 5/0634* (2013.01); *G01N 33/56966* (2013.01)

(58) Field of Classification Search
None
See application file for complete search history.

(56) References Cited

U.S. PATENT DOCUMENTS

| | | | |
|---|---|---|---|
| 6,184,011 B1 * | 2/2001 | Siegel | C12N 11/10 435/173.1 |
| 6,378,527 B1 * | 4/2002 | Hungerford | A61K 9/1652 128/898 |
| 7,595,043 B2 * | 9/2009 | Hedrick et al. | 424/93.7 |
| 2002/0164825 A1 * | 11/2002 | Chen | 436/526 |
| 2005/0100877 A1 * | 5/2005 | Xu et al. | 435/2 |
| 2008/0124721 A1 * | 5/2008 | Fuchs et al. | 435/6 |

FOREIGN PATENT DOCUMENTS

WO    WO 9604302 A1 *   2/1996

OTHER PUBLICATIONS

Ghosh et al. "Conformational contraction and hydrolysis of hyaluronate in sodium hydroxide solutions", Macromolecules 26: 4685-93, 1993.*
Diez-Silva et al. "Shape and biomechanical charateristics of human red blood cells in health and disease", MRS Bull 35(5): 382-388, 2010.*

* cited by examiner

*Primary Examiner* — Emily Cordas
(74) *Attorney, Agent, or Firm* — Blank Rome LLP

(57) ABSTRACT

Methods for recovering target cells using degradable three dimensional matrices are described.

12 Claims, 5 Drawing Sheets

METHODS FOR OBTAINING TARGET CELLS

CROSS-REFERENCE TO RELATED APPLICATIONS

This application claims priority based on PCT/US2011/060984, filed Nov. 16, 2011, and U.S. Provisional Application Ser. No. 61/414,329, filed Nov. 16, 2010, both of which are incorporated herein by reference in their entireties.

TECHNICAL FIELD

This invention relates to methods and materials for obtaining target cells from a fluid, cell-containing sample, and more particularly to obtaining target cells from a fluid, cell-containing sample using a matrix that retains target cells and that can be degraded to recover the target cells.

BACKGROUND

Despite considerable progress in diagnosing and treating solid tumors, metastatic disease remains the foremost cause of cancer-related death. While metastasis is widely considered as a late event in the evolution of malignant tumors, cells can disseminate from tumors in even the earliest stages of cancer progression. See e.g. Weinberg, *Cancer Cell* 14(4):283 (2008); Podsypanina et al., *Science* 321(5897):1841 (2008); Riethmüller et al., *Cancer Cell* 13(1):58 (2008). Although the mechanisms of metastasis development are yet to be fully elucidated, circulation of tumor cells within the blood is considered a fundamental intermediate event in the metastatic cascade. In addition, disseminated tumor cells ("DTC") are believed to home to the bone marrow in various solid tumors of epithelial origin and the bone marrow thus becomes an occult reservoir of tumor cells.

With current diagnostic approaches, the spread of tumor cells in most patients is undetected until after metastatic disease is well-established, and early, potentially effective, intervention is not an option. In addition, most therapeutic decisions are presently informed by metrics that mainly reflect the nature of the primary tumor. See Fischer, *Arch. Pathol. Lab. Med.* 133(9):1367 (2009). However, as evidenced by therapeutic resistance, tumor genotype and phenotype often change over the course of treatment. Circulating tumor cells ("CTC") function as immediate indicators of tumor load and character, and evaluation of CTCs provides real-time information regarding treatment efficacy. See Mostert et al., *Cancer Treat. Rev* 35(5):463 (2009). Introduction of a facile means for the early detection and continual systemic monitoring of circulating tumor cells would allow timely administration of a wider range of treatment options that are more appropriately tailored to a patient's specific disease as indicated by the changing characteristics of both the primary tumor, and just as importantly, nascent metastases.

SUMMARY

This document is based on the discovery of a method for obtaining target cells using a degradable three-dimensional matrix. The three-dimensional structure of the matrix provides a large surface area for capture of the target cells. Degrading the matrix allows cells retained by the matrix to be recovered. Cells recovered using the methods described herein can be used for tissue culture, diagnostic testing, further purification, or therapeutic administration.

In one aspect, this document features a method for obtaining target cells from a fluid, cell-containing sample. The method includes providing the fluid, cell-containing sample; passing the sample through a degradable, three-dimensional matrix, wherein the matrix has a structure that retains target cells; and recovering target cells retained within the matrix by substantially degrading the matrix. The fluid, cell-containing sample can be a blood sample, bone marrow aspirate, lymph, cerebral spinal fluid, ductal fluid, or needle biopsy aspirate. For example, the fluid, cell-containing sample can be a peripheral blood or umbilical cord blood sample. The fluid, cell-containing sample can be the fluid portion of a lipoaspirate. The matrix can be composed of collagen or gelatin. The matrix can be composed of a polysaccharide selected from the group consisting of hyaluronic acid, chitosan, cellulose, and alginate. The matrix can be composed of a degradable natural or synthetic polymer (e.g., a polyester such as a polylactide, polycaprolactone, or polyglycolic acid). Degrading the matrix can include contacting the matrix with a degradative enzyme for an amount of time sufficient to sufficiently degrade the matrix. The degradative enzyme can be a collagenase, hyaluronidase, or protease. In some embodiments, the polysaccharide is hyaluronic acid and degrading the matrix include contacting said matrix with a hyaluronidase for an amount of time sufficient to degrade said matrix. Degrading the matrix can include contacting the matrix with an acidic or basic solution for an amount of time sufficient to sufficiently degrade the matrix. The method further can include concentrating the cells recovered from the matrix. A pump can be used to pass the sample through the matrix.

In another aspect, this document features a method for obtaining target cells from a fluid, cell-containing sample. The method includes providing the fluid, cell-containing sample; passing the sample through a degradable, three-dimensional matrix, wherein the matrix includes a capture ligand attached thereto, the capture ligand having affinity for a target cell in the sample; and recovering target cells retained by the matrix by substantially degrading the matrix. The capture ligand can be an antibody or an antigen binding fragment thereof (e.g., a Fab, F(ab')2, Fv, or single chain Fv (scFv) fragment). The antibody or antigen binding fragment thereof can have binding affinity for a cell surface molecule on a tumor cell. The cell surface molecule can be a cell adhesion molecule. The cell surface molecule can be epithelial cell adhesion molecule (EpCAM), mucin 1 (MUC1), Human Epidermal growth factor Receptor 2 (HER2), or Melanoma-associated Chondroitin Sulfate Proteoglycan (MCSP). The antibody or antigen binding fragment thereof can have binding affinity for CD71, CD36, CD45, glycophorin A, CD35, CD47, SSEA-4, CD117, or CD146. In some embodiments, at least two different capture ligands are attached to the matrix. The at least two different capture ligands can have binding affinity for two different cell surface molecules selected from the group consisting of CD71, CD36, CD45, glycophorin A, CD35, CD47, SSEA-4, CD117, or CD146. For example, the two different cell surface molecules can be selected from the group consisting of CD71, CD36, CD45, glycophorin A, CD35, and CD47. In some embodiments, the capture ligand is a lectin (e.g., soybean agglutinin (SBA), peanut agglutinin (PNA), *Erythrina cristagalli* lectin (ECL), *Allomyrina dichotoma* lectin (Allo A), *Viscum album* agglutinin (VAA), concanavalin A (Con A), *Lens culinaris* lectin (LcH), and *Pisum sativum* agglutin (PSA). The target cells can be circulating tumor cells, disseminated tumor cells, embryonic cells, or fetal red blood cells. In some embodiments, the fluid, cell-containing sample is depleted of erythrocytes. The method further can include concentrating the cells recovered from the matrix. A pump can be used to pass the sample through the matrix.

This document also features a method for obtaining target cells from a fluid, cell-containing sample. The method includes providing said fluid, cell-containing sample; passing the sample through a three-dimensional matrix, the matrix comprising an inner core and an outer layer disposed around the inner core, the inner core comprising a non-degradable substrate, the outer layer composed of a degradable polymer and having a structure that retains target cells; and recovering target cells retained by the matrix by substantially degrading the outer layer of the matrix. The inner core can be composed of woven or non-woven polypropylene, nylon, silk mesh, or fabric. The method further can include concentrating the cells recovered from the matrix. A pump can be used to pass the sample through the matrix.

This document also features a method for obtaining target cells from a fluid, cell-containing sample. The method includes providing the fluid, cell-containing sample; passing the sample through a three-dimensional matrix, the matrix comprising an inner core and an outer layer disposed around the inner core, the inner core comprising a non-degradable substrate, the outer layer composed of a degradable polymer, wherein the outer layer comprises a capture ligand attached thereto, the capture ligand having affinity for a target cell in the sample; and recovering target cells retained by the matrix by substantially degrading the outer layer of the matrix. The inner core can be composed of woven or non-woven polypropylene, nylon, silk mesh, or fabric.

In another aspect, this document features a method for obtaining target cells in a fluid, cell-containing sample. The method includes removing erythrocytes from the fluid, cell-containing sample to produce an erythrocyte depleted sample; passing the erythrocyte depleted sample over a degradable three-dimensional matrix, wherein the matrix comprises a capture ligand attached thereto, the capture ligand having affinity for target cells in the sample; and recovering target cells retained by the matrix by substantially degrading the matrix. The capture ligand can be a lectin, or an antibody or an antigen binding fragment thereof as discussed herein. The method further can include concentrating the cells recovered from the matrix. A pump can be used to pass the sample through the matrix.

In any of the methods described herein, the fluid, cell-containing sample can be centrifuged to fractionate cells according to their respective specific gravity before passing one or more of the cell fractions over the degradable three dimensional matrix.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the exemplary methods and materials are described below. All publications, patent applications, patents, Genbank® Accession Nos, and other references mentioned herein are incorporated by reference in their entirety. In case of conflict, the present application, including definitions, will control. The materials, methods, and examples are illustrative only and not intended to be limiting.

Other features and advantages of the invention will be apparent from the following detailed description, and from the claims.

DETAILED DESCRIPTION

In general, this document is based on an affordable point-of-use platform for the rapid isolation of target cells from fluid, cell-containing samples. As used herein, "fluid, cell-containing sample" refers to a liquid containing a suspension of cells. Non-limiting examples of such fluid, cell-containing samples include blood samples (e.g., peripheral blood or umbilical cord blood), the liquid fraction of a lipoaspirate, bone marrow aspirates, lymph, cerebral spinal fluid, ductal fluid, or needle biopsy aspirates. Such fluid, cell-containing samples can be obtained from any mammalian subject, including humans, monkeys, mice, rats, rabbits, guinea pigs, dogs, or cats. In some embodiments, the cells from a sample such as blood sample can be washed (e.g., with phosphate buffered saline) and resuspended in saline, physiological buffer, or culture medium before processing as described herein. In some embodiments in which the fluid, cell-containing sample contains erythrocytes, the erythrocytes can be removed by, for example, density gradient sedimentation or hetastarch aggregation.

Target cells retained by the matrix are viable and can be used for any purpose, including tissue culture, characterization, diagnostic testing, or further purification. Target cells found in fluid, cell-containing samples can include, for example, fetal blood cells, white blood cells, circulating tumor cells, disseminated tumor cells, stem cells, or bacteria (e.g., Staphylococcus or Streptococcus). For example, in some embodiments, fetal blood cells can be recovered from a sample of maternal blood and used for non-invasive prenatal diagnosis. Stem cells can be recovered from, for example, a sample of umbilical cord blood. Circulating tumor cells or disseminated tumor cells can be recovered from a fluid, cell-containing sample (e.g., peripheral blood, bone marrow, or lymph) to detect metastasis in a patient, determine prognosis in patients, or test for drug resistance. Bacteria can be removed from a fluid, cell-containing sample (e.g., peripheral blood sample) to detect sepsis.

Three Dimensional Matrices

Figure 1A:
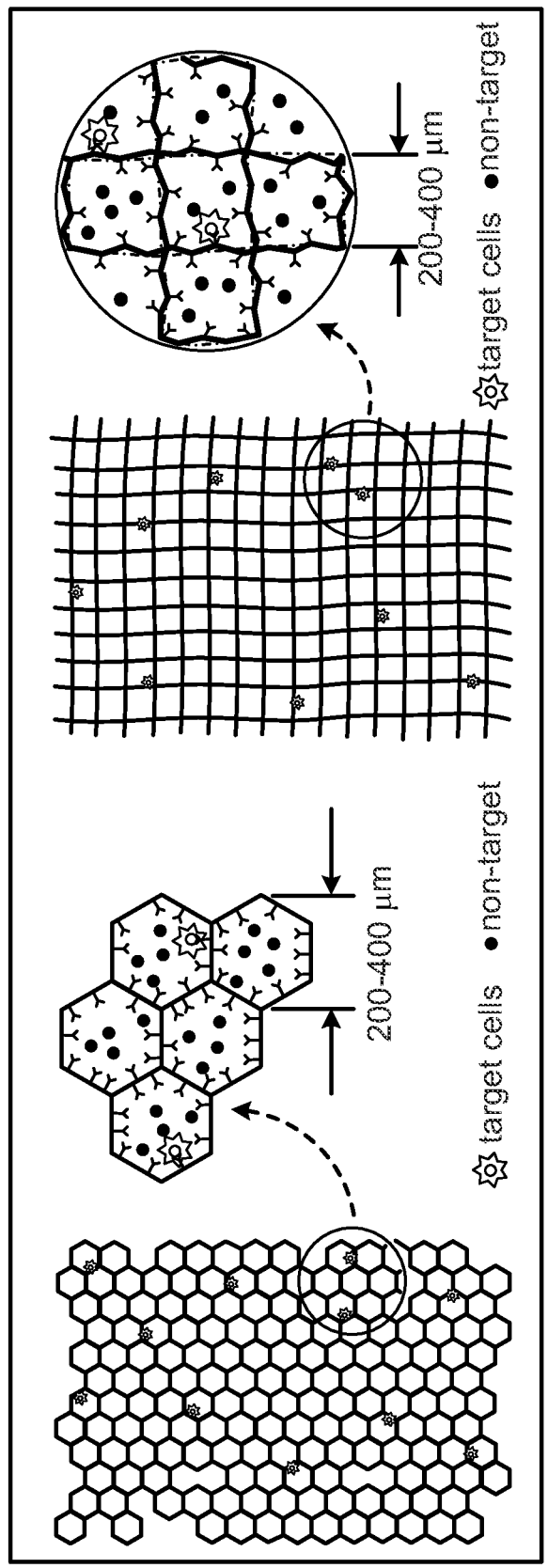
FIG. 1A is a schematic diagram of two embodiments of a matrix. The left panel is a representation of a two dimensional section through a three dimensional matrix having a honeycomb pattern. The right panel is a representation of a two dimensional section through a three dimensional matrix having a grid-like pattern.

As used herein, suitable three dimensional matrices have a structure that retains target cells and/or contains a capture ligand that has binding affinity for target cells. For suitable three dimensional matrices described herein, no dimension of the matrix is less than 0.5 µM, providing a large surface area for capture of target cells. In some embodiments, a three dimensional matrix can have a porosity (e.g., <10 μM) that retains cells of a certain size (e.g., white blood cells) while allowing others (e.g., erythrocytes and platelets) to pass through the matrix. See, for example, FIG. 1A for a schematic representation of a two dimensional section through a three dimensional matrix having either a honeycomb or a grid-like pattern.

In some embodiments, a three dimensional matrix contains a capture ligand attached thereto, where the capture ligand has affinity for a target cell in the sample. In some embodiments, the capture ligand is indirectly attached to the three dimensional matrix via, for example, avidin or streptavidin. For example, a three dimensional matrix can be functionalized with avidin or streptavidin, and a capture ligand can be biotinylated.

A capture ligand can have binding affinity for one or more cell surface molecules on a tumor cell. A cell surface molecule can be a cell adhesion molecule. In some embodiments, the cell surface molecule is epithelial cell adhesion molecule (EpCAM), mucin 1 (MUC1), human epidermal growth factor receptor 2 (HER2), or Melanoma-associated chondroitin sulfate proteoglycan (MCSP).

A capture ligand also can have binding affinity for one or more cell surface molecules (e.g., two different cell surface molecules) on a fetal blood cell. For example, a capture ligand can have binding affinity for one or more of CD71, CD36, CD45, glycophorin A, CD35, and CD47. Such cell surface molecules are found on fetal erythroblasts. See, for example, Ho et al., *Ann Acad Med Singapore* 32:597-604 (2003). In some embodiments, a capture ligand has binding affinity for SSEA-4, CD117, or CD146.

A capture ligand can be an antibody or antigen-binding fragment thereof that has binding affinity for a target cell in the sample. In some embodiments, a suitable antibody or antigen-binding fragment thereof also can have affinity for immunoglobulin (e.g., anti-IgG antibody). "Antibody" as the term is used herein refers to a protein that generally includes heavy chain polypeptides and light chain polypeptides. IgG, IgD, and IgE antibodies comprise two heavy chain polypeptides and two light chain polypeptides. IgA antibodies comprise two or four of each chain and IgM generally comprise 10 of each chain. Single domain antibodies having one heavy chain and one light chain and heavy chain antibodies devoid of light chains are also contemplated. A given antibody comprises one of five types of heavy chains, called alpha, delta, epsilon, gamma and mu, the categorization of which is based on the amino acid sequence of the heavy chain constant region. These different types of heavy chains give rise to five classes of antibodies, IgA (including IgA1 and IgA2), IgD, IgE, IgG (IgG1, IgG2, IgG3 and IgG4) and IgM, respectively. A given antibody also comprises one of two types of light chains, called kappa or lambda, the categorization of which is based on the amino acid sequence of the light chain constant domains.

"Antigen binding fragment" refers to an antigen binding molecule that is not an antibody as defined above, but that still retains at least one antigen binding site. Antibody fragments often comprise a cleaved portion of a whole antibody, although the term is not limited to such cleaved fragments. Antigen binding fragments can include, for example, a Fab, F(ab')2, Fv, and single chain Fv (scFv) fragment. An scFv fragment is a single polypeptide chain that includes both the heavy and light chain variable regions of the antibody from which the scFv is derived. Other suitable antibodies or antigen binding fragments include linear antibodies, multispecific antibody fragments such as bispecific, trispecific, and multispecific antibodies (e.g., diabodies (*Poljak Structure* 2(12):1121-1123 (1994); Hudson et al., *J. Immunol. Methods* 23(1-2):177-189 (1994)), triabodies, tetrabodies), minibodies, chelating recombinant antibodies, intrabodies (Huston et al., *Hum. Antibodies* 10(3-4):127-142 (2001); Wheeler et al., *Mol. Ther.* 8(3):355-366 (2003); Stocks *Drug Discov. Today* 9(22): 960-966 (2004)), nanobodies, small modular immunopharmaceuticals (SMIP), binding-domain immunoglobulin fusion proteins, camelid antibodies, camelized antibodies, and VHH containing antibodies.

A capture ligand also can be a lectin having binding affinity for a sugar moiety that is on a glycoprotein or glycolipid. For example, the lectin can be soybean agglutinin (SBA), peanut agglutinin (PNA), *Erythrina cristagalli* lectin (ECL), *Allomyrina dichotoma* lectin (Allo A), *Viscum album* agglutinin (VAA), concanavalin A (Con A), *Lens culinaris* lectin (LcH), or *Pisum sativum* agglutin (PSA). SBA, PNA, ECL, Allo A, and VAA have binding affinity for galactose moieties while ConA, LcH, and PSA have binding affinity for glucose moieties.

Materials that can be used to fabricate a three dimensional matrix for use in the methods described herein can be generally categorized into two types: naturally derived materials (e.g., polymers) and synthetic materials (e.g., polymers). Non-limiting examples of naturally derived polymers include extracellular matrix (ECM) molecules (e.g., collagens, hyaluronic acid, or laminins) or products thereof (e.g., gelatin, which is partially hydrolyzed collagen), and polysaccharides (e.g., alginate, chitin, chitosan, agarose, or cellulose). Any such matrix, and blends of these materials with other polymers or other materials, is contemplated for use in the methods described herein. In one embodiment, the three dimensional matrix is a laminin rich gel.

Type I collagen, the most prevalent ECM molecule in the body, is readily isolated from animal tissues, or can be produced using recombinant DNA technology, and can be processed into a wide variety of structures for use in the methods described herein. For example, collagen can be woven into a three-dimensional framework such as a collagen sponge. Three dimensional matrices with a sponge-like structure also can be produced through lyophilization of collagen solutions, including reproducibly adjusting the mean pore size and geometry of such collagen sponges according to freeze-drying parameters. O'Briena et al., *Biomaterials* 6:1077-1086 (2004). As a biopolymer, collagen also is amenable to functionalization including with antibodies or other ligands using standard EDC (carbodiimide)/NHS mediated crosslinking approaches. See Kojima et al., *Biomaterials* 27(28): 4904 (2006). The structure and resultant mechanical properties of collagen-based matrices can be regulated by the process utilized to extract the collagen from tissues and by various crosslinking processes. Collagen molecules can be crosslinked physically by dehydrothermal or UV radiation treatments, or chemically by using various chemical agents. Suitable collagen matrices are described, for example, in U.S. Pat. No. 5,885,829

In some embodiments, the three dimensional matrix is composed of one or more synthetic polymeric materials. Synthetic polymers can be processed with various techniques. The mechanical and physical properties of synthetic polymers can be readily adjusted through variation of molecular structures. Non-limiting examples of suitable synthetic polymers that are degradable include polyesters such as poly(glycolic acid) (PGA), poly(lactic acid) (PLA), poly(lactic acid)-poly(glycolic acid) (PLGA) polymers, polyhydroxybutyrate (PHB), or other polyhydroxyalkanoates. Further degradable matrices include polyanhydrides, polyorthoesters, and poly(amino acids). Any such matrix may be utilized to fabricate a three dimensional matrix having a structure that retains target cells or that can be derivatized. See, for example, U.S. Pat. No. 5,885,829 for suitable synthetic polymer matrices.

In some embodiments, a three-dimensional matrix contains an inner core and an outer layer disposed around the inner core. The outer layer is composed of a degradable polymer as described above and has a structure that retains target cells and/or contains a capture ligand. In such an embodiment, the inner core is composed of a substrate that differs from the outer layer and is not-degradable in the same manner as the outer layer. For example, the inner core can be woven or non-woven polypropylene, nylon, silk mesh, or fabric.

Figure 1B:
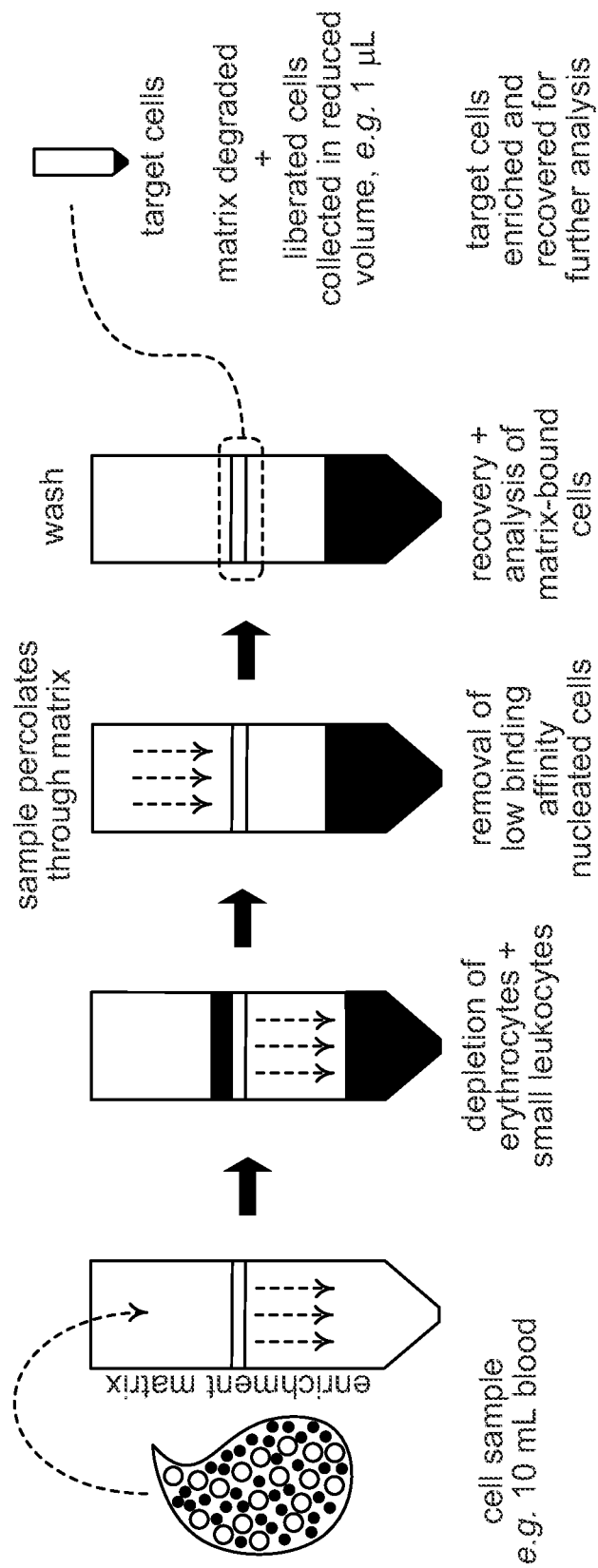
FIG. 1B is a schematic diagram of a method of obtaining target cells using a three dimensional matrix within a conical tube.

In some embodiments, the three dimensional matrix is adapted in the form of an insert that can be fitted into a standard conical tube (e.g., a 15 or 50 mL centrifuge tube) See, for example, FIG. 1B. After passing a fluid, cell-containing sample through the matrix within such a tube, the cells are trapped within the matrix while the non-target cells (e.g., red blood cells and platelets) are in the lower portion of the tube. The matrix can be further washed with a buffer. In some embodiments, a pump can be used to pass the sample through the matrix.

Target cells can be recovered from a matrix by substantially degrading the matrix. As used herein, the term "substantially degrading" with reference to the matrix indicates at least 50% (e.g., at least 55%, 60%, 70%, 75%, 80%, 85%, or 90%) of the matrix has been degraded. For example, the matrix can be contacted with a degradative enzyme for an amount of time sufficient to degrade the matrix. Non-limiting examples of degradative enzymes include collagenase, hyaluronidase, proteases, chitosanase, alginate lyase, alginate depolymerase, and cellulase. For example, if the three dimensional matrix contains hyaluronic acid, the matrix can be degraded by contacting the matrix with a hyaluronidase for an amount of time sufficient to substantially degrade the matrix. If the degradable matrix is a protein a protease can be used to substantially degrade the matrix. In some embodiments, degrading the matrix can include contacting the matrix with an acidic or basic solution for an amount of time sufficient to substantially degrade the matrix.

The amount of time sufficient to substantially degrade the matrix can be determined empirically by one of ordinary skill in the art for the matrix employed. Factors such as type and concentration of enzyme, temperature and presence of chelation agents relative to required enzyme cofactors, and incubation time can be varied to determine the amount of time to degrade the matrix.

After degrading the matrix, cells can be recovered using, for example, centrifugation.

Articles of Manufacture

This document also features articles of manufacture that include three dimensional matrices described herein. Three dimensional matrices can be combined with packaging material and sold as a kit. For example, a kit can include a three dimensional matrix derivatized with one or more ligands for capture of target cells (e.g., fetal cells from maternal blood or circulating tumor cells). A kit further can include one or more of an apparatus for sample collection such as a vacutainer blood collection tube and needle, a cryopreservative, culture medium, or reagents for characterizing the target cells. The packaging material included in a kit typically contains instructions or a label describing how the three dimensional matrix can be used to recover and/or preserve target cells from a fluid, cell-containing sample. Components and methods for producing such kits are well known.

The following are examples of the practice of the invention. They are not to be construed as limiting the scope of the invention in any way.

EXAMPLES

Example 1: Recovery of Cells Using a Degradable Matrix

In this experiment, a collagen sponge (PURACOL® PLUS™ microscaffold collagen wound dressing, 10 mm diameter) was used to recover white blood cells (WBC) from a test sample where the ratio of red blood cells (RBC) to WBC was 1000:1. The collagen sponge was placed in a SWINNEX® brand 10 mm membrane filter unit. The test sample was passed through the sponge, which then was gently rinsed by flushing with 3 mL of sterile phosphate buffered saline (PBS) at 200 µl/min. The collagen sponge then was removed from the filter unit and placed in a 35 mm culture dish containing 3 mL of sterile lactated Ringer's with 1.2 units/mL collagenase IV (CLS-4, Worthington Biochemicals, Lakewood, N.J.). The sponge was incubated at 37° C. with rotational shaking (approximately 60 rpm) for 30 min or until the sponge was digested. The contents of the culture dish were removed by pipette and placed into a 15 mL sterile conical centrifuge tube. Cells were recovered by centrifuging the tube at 400×g for 5 min. Cells were washed 3× with 3 mL PBS to remove collagenase and then resuspended in desired buffer or media. Table 1 provides the estimated WBC recovery and RBC depletion factor at various dilutions, wash volumes, and flow rates.

TABLE 1

| blood volume, µL | ringers, µL | Dilution | wash volume, µL | flow rate µL/min | estimated WBC recovery | RBC:WBC on filter | RBC depletion factor |
|---|---|---|---|---|---|---|---|
| 200 | 800 | 1/5 | 1000 | 1000 | 2.75% | 9.9 | 101 |
| 20 | 980 | 1/50 | 1000 | 1000 | 5.00% | 12.0 | 83 |
| 200 | 800 | 1/5 | 1000 | 100 | 24.50% | 10.0 | 100 |
| 200 | 0 | neat | 1800 | 1000 | 2.50% | 102.0 | 10 |

Example 2: Preparation of a Collagen Three-Dimensional Matrix

A high-surface-area, three-dimensional matrix can be made from reconstituted type I bovine collagen as set forth in O'Briena et al., *Biomaterials*, 6:1077-1086 (2004). To determine if a matrix is suitable for enriching for cells, 5-40 mL samples of blood and various cell suspensions can be passed through the filter and processed as described in Example 1. Samples were successfully processed without noticeable clogging of commercially obtained collagen matrices, resulting in a depletion of approximately 85% of the erythrocytes and retention of almost 100% of the nucleated cells.

In enrichment experiments with heterogeneous mixtures of human nucleated cells, high-affinity, preferential attachment of stromal cells was attained compared to circulating leukocytic cells normally present in blood, without the use of capture antibodies.

Example 3: Recovery of Ramos Tumor Cells

Figure 2:
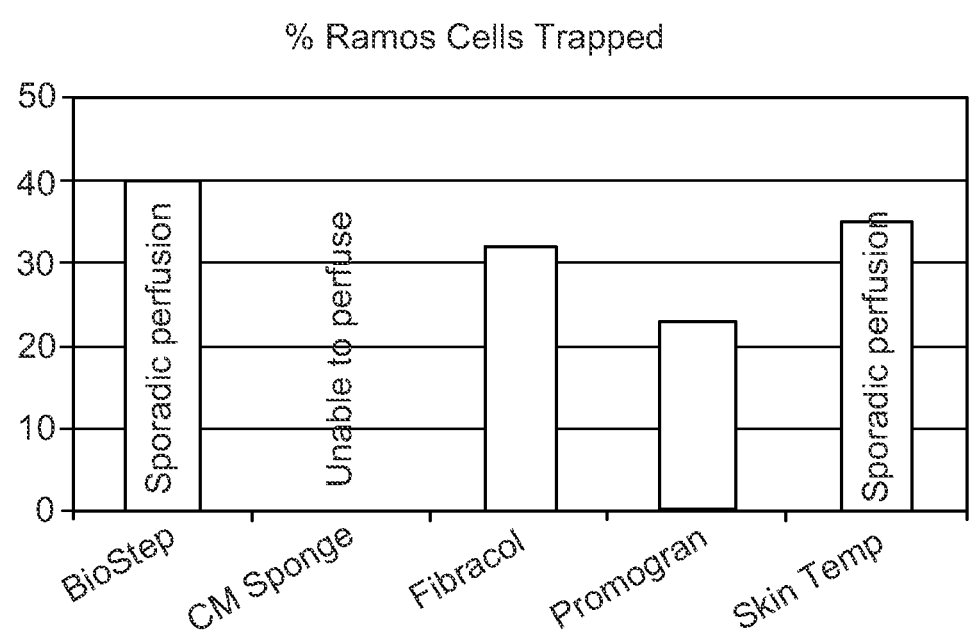
FIG. 2 is a graph of the percentage of Ramos tumor cells trapped using the following collagen matrices: BIOSTEP®, CM SPONGE®, FIBRACOL®, PROMOGRAN®, and SKIN TEMP®.

This example describes the recovery of Ramos tumor cells using the following collagen matrices: BIOSTEP® brand collagen matrix dressing (Smith & Nephew), MATRIX COLLAGEN SPONGE™ brand wound dressing formed from purified, type I collagen in its native helical structure ("CM," Collagen Matrix, Inc.), FIBRACOL® brand collagen wound dressing (Johnson & Johnson), PROMOGRAN® brand wound dressing (Allegro Medical), and SKINTEMP® brand collagen dressing (Medifil). One×$10^6$ cells of Ramos tumor cells in suspension were loaded onto each matrix at 1 mL/minute. The collagen matrices were degraded using 2 U/ml collagenase, 100 U/ml DISPASE® brand neutral protease (Roche Industrial Enzymes). FIG. 2 is a graph that shows the percentage of total Ramos cells trapped using the matrices. The CM sponge was not suitable as it could not be perfused. While the BIOSTEP® brand and SKINTEMP® brand matrices retained a high percentage of tumor cells, perfusion was sporadic.

Figure 3A:
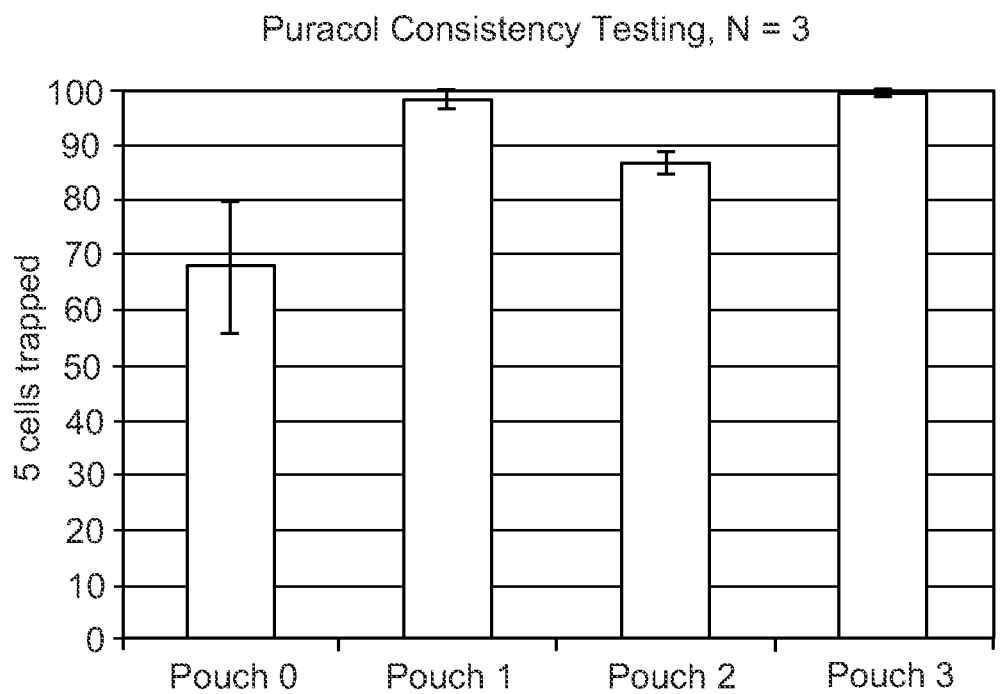
FIGS. 3A and 3B are graphs of the percentage of Ramos cells trapped on PURACOL® PLUS™ microscaffold collagen wound dressing.
Figure 3B:
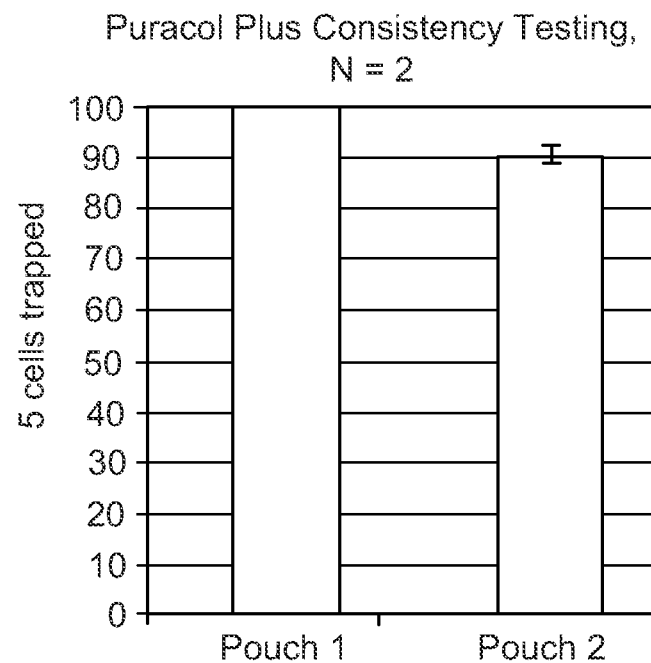

A similar experiment was repeated using the Ramos tumor cells and PURACOL® PLUS™ microscaffold collagen wound dressing (Medline). FIG. 3 is a graph that shows the high percentage of trapped Ramos cells using the PURACOL® PLUS™ microscaffold collagen wound dressing.

Example 4: Recovery and Culture of Human Adipose Derived Stromal Cells (ADSCs)

Fresh human ADSCs were prepared from lipoaspirate by enzymatic digestion with a collagenase: DISPASE® blend (2 U/ml collagenase, 100 U/ml DISPASE® brand neutral protease; Roche Industrial Enzymes) in Ringer's lactate, filtration through 100 μm mesh, and 3× centrifugation and resuspension in cell growth media (MEM, 20% FBS) at $10^5$ nucleated cells/mL. One mL ($10^5$ cells) or 5 mL (5×$10^5$ cells) cells were loaded onto a 1 cm diameter PURACOL® PLUS™ brand collagen sponge by passage through a SWINNEX® brand filter assembly in which one or two 2 mm thick PURACOL® PLUS™ disks had been placed. After loading, a sample of media that passed through the sponge was collected for cell count, and the remainder was centrifuged, resuspended in 2 mL growth media and plated (12 well plate). Loaded collagen disks were placed in 2 mL media and cultured in the same plate. Media was changed after 24 h. Approximately 120 h after initiation of culture, cells in monolayer (i.e., grown from the media that passed through the sponge) and cells on PURACOL®PLUS™ disks were washed 3× with 2 mL Hank's Buffered Salt Solution (HBSS). Cells in monolayer were photographed under light microscope, detached by trypsinization with EDTA and counted. Cells on PURACOL® PLUS™ were released by digestion of PURACOL® PLUS™ for 30 min at 37° C. with collagenase: DISPASE® in Ringer's lactate. Cells were recovered by centrifugation and washed 3×HBSS before resuspension in 2 mL culture media. Cell count was obtained, and then cells were plated onto plastic (12 well plate) and photographed approximately 6 h later. The results are depicted in Table 2.

TABLE 2

| Condition | Cells not captured | Cells captured | Cells at 120 h on plate | Cells at 120 h in PURACOL® PLUS™ |
|---|---|---|---|---|
| 2 mm, $10^5$ cells | 62000 | 38000 | 210000 | 237500 |
| 2 mm, 5 × $10^5$ cells | 460000 | 40000 | 617500 | 225000 |
| 2 × 2 mm, $10^5$ cells | 0 | 100000 | 2500 | 175000 |
| 2 × 2 mm, 5 × $10^5$ cells | 230000 | 270000 | 397500 | 222500 |

Example 5: Determining Degradation Time of Matrix

Figure 4:
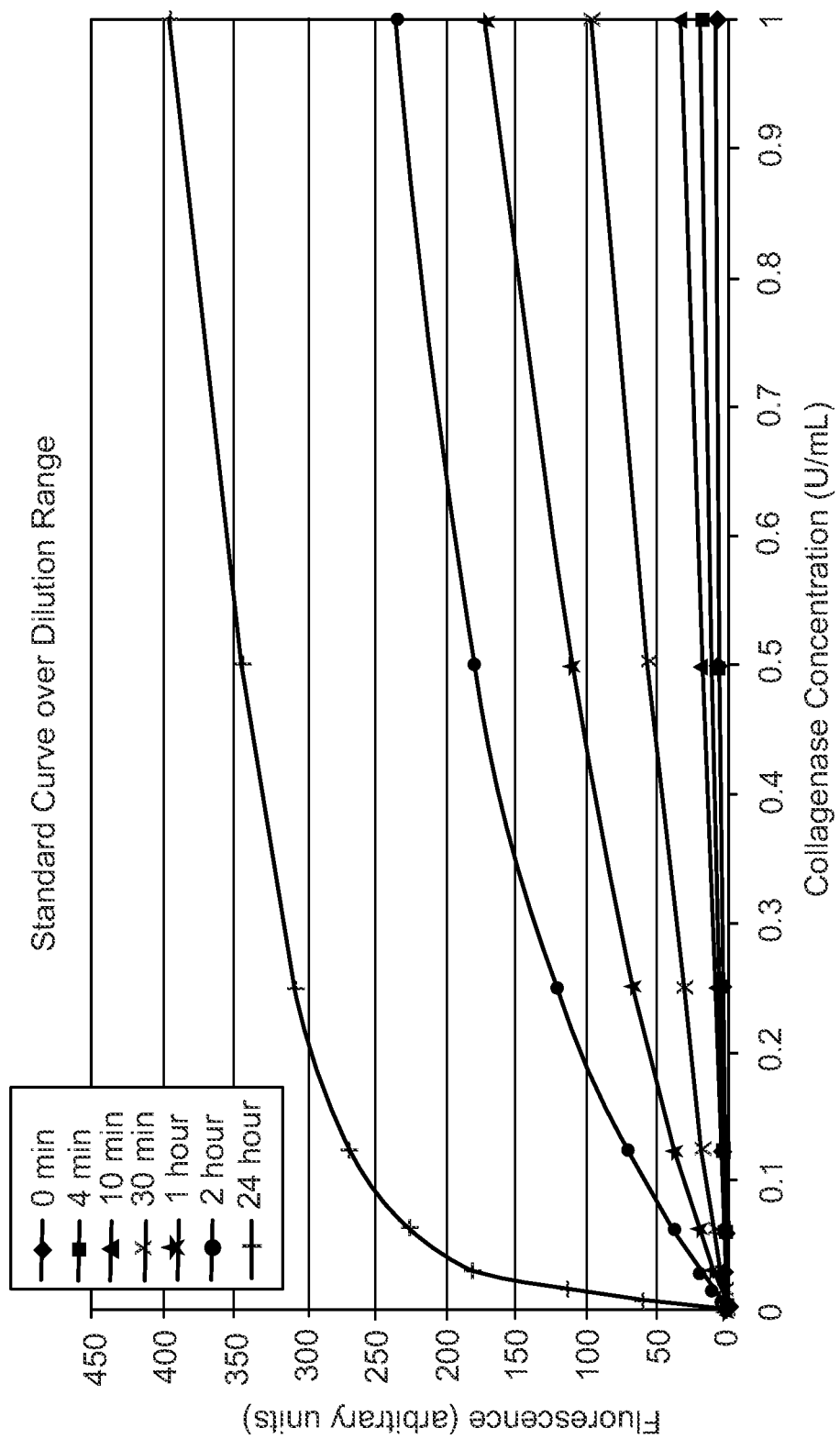
FIG. 4 is a graph of the amount of fluorescence as a function of collagenase concentration over different incubation periods (0 min, 4 min, 10 min, 30 min, 1 hr, 2 hr, or 24 hr) for gelatin beads (Cultispher) loaded with fluorescein.

Titration curves of enzyme (e.g., collagenase or protease) concentration versus time can be developed for a given matrix as exemplified in FIG. 4 for gelatin beads (CULTISPHER®) loaded with fluorescein. The fluorescence of the fluorescein is quenched within the beads. Upon digestion of the bead with the enzyme (e.g., a protease or collagenase), fluorescein is released.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for obtaining target cells from a fluid, cell-containing sample, the method comprising:
    a) providing a fluid, cell-containing sample;
    b) passing the sample through a degradable matrix filter mounted as an insert in a conical tube or filter unit, the filter having a three dimensional structure that is fabricated of an enzyme degradable biopolymer, wherein the matrix filter has a porosity that physically retains target cells based on a size of the target cells while allowing passage of smaller non-target cells, including erythrocytes, through the matrix filter;
    c) removing the filter from the conical tube or filter unit and recovering target cells retained within the matrix filter by enzymatically degrading said matrix filter such that at least 50% of the three dimensional structure of the matrix filter is enzymatically degraded such that the three dimensional structure is no longer able to physically retain the target cells; and
    d) recovering the target cells from the enzymatically degraded matrix filter by centrifugation.

2. The method of claim 1, wherein the fluid, cell-containing sample is peripheral blood, umbilical blood, bone marrow aspirate, lymph, cerebral spinal fluid, ductal fluid, needle biopsy aspirate, or lipoaspirate.

3. The method of claim 1, wherein the matrix comprises one or more of collagen, hyaluronic acid, laminin, chitosan, cellulose, alginate and products of each of collagen, hyaluronic acid, laminin, chitosan, cellulose, and alginate.

4. The method of claim 1, wherein degrading the matrix comprises contacting the matrix with a collagenase, hyaluronidase, or protease for an amount of time sufficient to digest at least 90% of the matrix filter.

5. The method of claim 1, wherein the matrix filter containing the physically trapped target cells is placed into culture to expand the cells prior to recovery of the cells by degrading the matrix.

6. The method of claim 1, wherein the matrix filter has at least one capture ligand attached to it prior to passing the sample through the matrix filter.

7. The method of claim 6, wherein at least one capture ligand is an antibody or an antigen binding fragment thereof has binding affinity for a cell surface molecule on the target cell.

8. The method of claim 7, wherein the cell surface molecule is epithelial cell adhesion molecule (EpCAM), mucin 1 (MUC1), Human Epidermal Growth Factor Receptor 2 (HER2), or Melanoma-associated Chondroitin Sulfate Proteoglycan (MCSP).

9. The method of claim 7, wherein the antibody or antigen binding fragment thereof has binding affinity for CD71, CD36, CD45, glycophorin A, CD35, CD47, Stage specific embryonic antigen-4 (SSEA-4), CD117, or CD146.

10. The method of claim 6, wherein at least one capture ligand is a lectin selected from the group consisting of soybean agglutinin (SBA), peanut agglutinin (PNA), *Erythrina cristagalli* lectin (ECL), *Allomyrina dichotoma* lectin (Allo A), *Viscum album* agglutinin (VAA), concanavalin A (Con A), *Lens culinaris* lectin (LcH), and *Pisum sativum* agglutin (PSA).

11. The method of claim 1, wherein the target cells are circulating tumor cells, disseminated tumor cells, embryonic cells, or fetal red blood cells.

12. The method of claim 1, wherein the fluid, cell-containing sample is a lipoaspirate.

* * * * *